United States Patent [19]

Rex et al.

[11] Patent Number: 4,592,745
[45] Date of Patent: Jun. 3, 1986

[54] DISPENSER

[75] Inventors: Jørn Rex, Roskilde; Otto A. Vogeley, Herlev, both of Denmark

[73] Assignee: Novo Industri A/S, Denmark

[21] Appl. No.: 584,876

[22] Filed: Feb. 29, 1984

[51] Int. Cl.⁴ ............................................. A61M 5/22
[52] U.S. Cl. ................................. 604/211; 604/224; 604/232; 604/152; 604/192
[58] Field of Search ........ 604/192, 193, 201, 207–211, 604/224, 232, 195, 93, 131, 152, 154, 155, 246; 128/DIG. 12; 222/390, 391

[56] References Cited

U.S. PATENT DOCUMENTS

| 3,200,486 | 8/1965 | Shields | 604/206 |
|---|---|---|---|
| 3,491,919 | 1/1970 | Ramsay | 222/390 |
| 3,790,048 | 2/1974 | Likiano et al. | 604/211 |
| 4,099,548 | 7/1978 | Sturm et al. | 604/209 |

FOREIGN PATENT DOCUMENTS

| 37696 | 3/1981 | European Pat. Off. |
| 82/02662 | 12/1982 | PCT Int'l Appl. |

*Primary Examiner*—Stephen C. Pellegrino
*Assistant Examiner*—Mark Rooney
*Attorney, Agent, or Firm*—Fidelman, Wolffe & Waldron

[57] ABSTRACT

An dispenser characterized by provision for use of a replaceable needle and a prefilled cartridge.

The dispenser comprises an elongated body separable into two body sections, with the front end section adapted to contain a prefilled cartridge and with provision at the front end for mounting a needle removably thereon.

The back end section contains the operating mechanism shown by FIG. 10 to convert the longitudinal movement of a pushable element into unidirectionally rotary movement, then into longitudinal movement of a piston rod that acts to expel fluid through the needle.

A multipurpose cap is protective of the needle end when mounted on the front end, and is an operating member when mounted on the rear end, as is illustrated by FIGS. 1 and 2.

10 Claims, 13 Drawing Figures

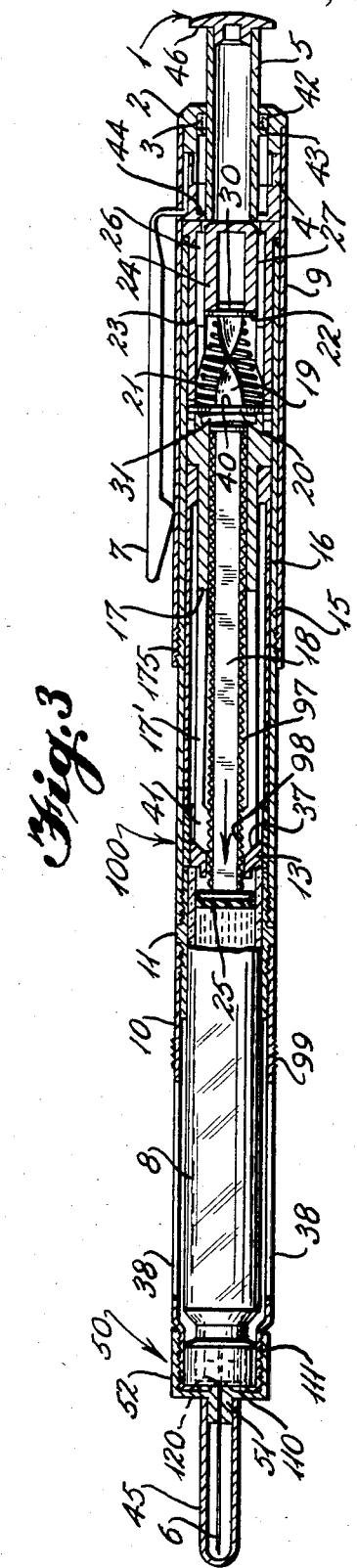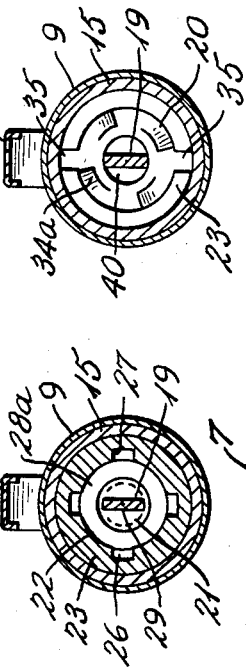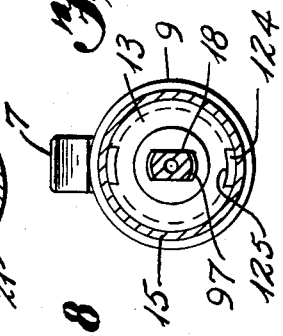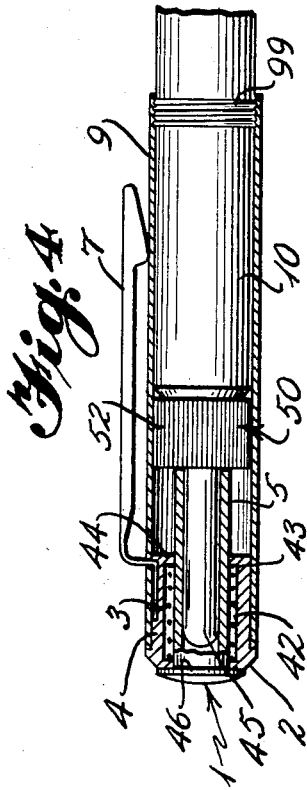

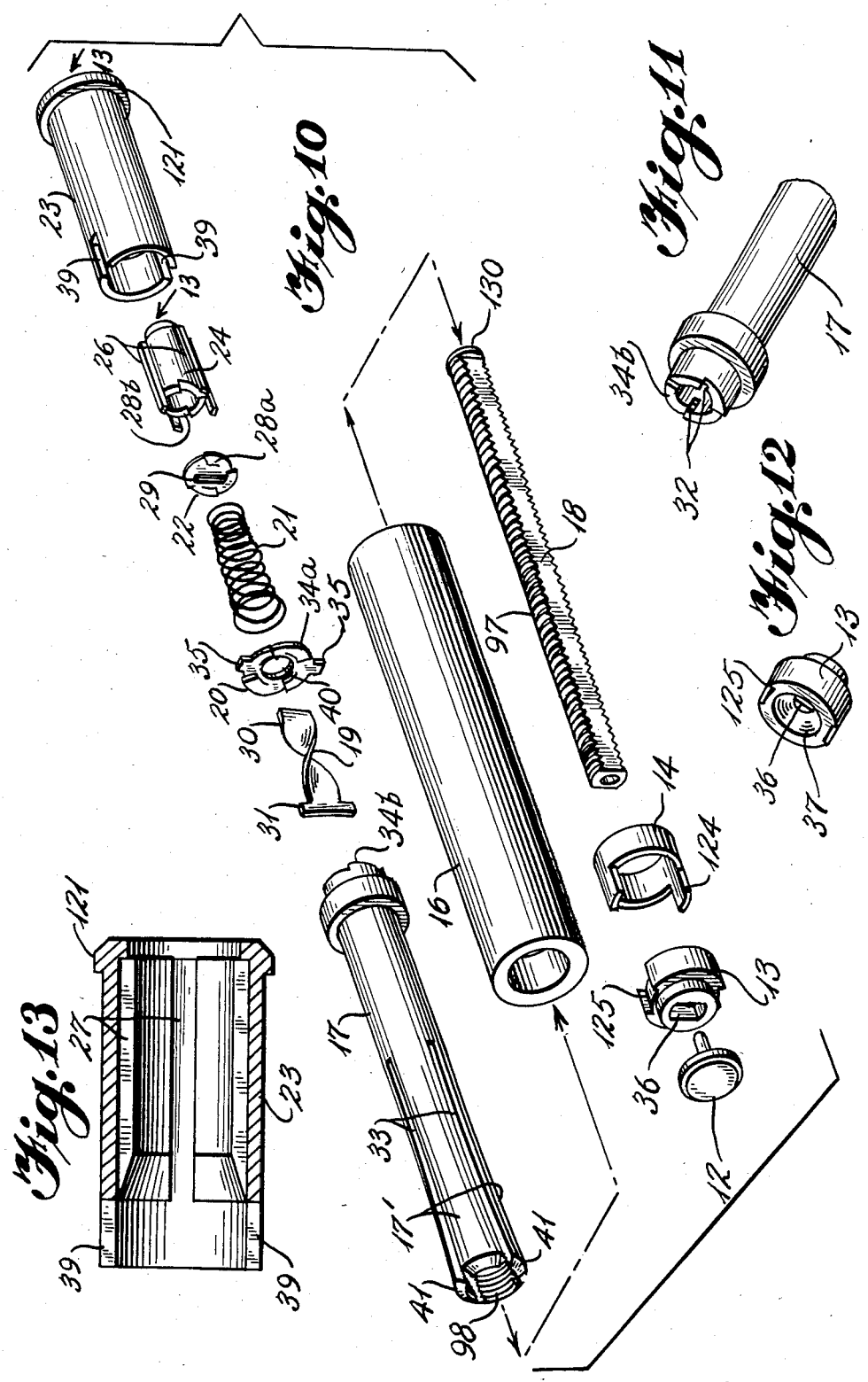

DISPENSER

INTRODUCTION

The present invention relates to a dispenser suitable for use in dispensing a liquid medicine, for instance insulin solution. The dispenser is, in principle, constructed as a hypodermic syringe but differs in that it enables dispensing of a predetermined portion from the available medicine, and in that it contains a separate reservoir member, and in that it dispenses very accurate dosages.

Since diabetics often require regular injections of the same or different amounts of insulin, employment of a conventional syringe is relatively cumbersome, as it is necessary to draw each injection dose into the syringe, check that the correct amount is in the syringe, and then inject the dose. Furthermore, precautions must be taken to expel all air from the syringe before injections.

The disadvantages of conventional syringes has been recognized by the art. European Patent Application (EPO) No. 37696, for example, describes a dispensing device for dispensing a predetermined quantity of a liquid from a multi-dose container wherein the liquid is expelled from the container by a plunger driven by unidirectional drive transmission means. Although the dispensing device of EPO No. 37696 enables successive injections of a predetermined quantity of fluid, the device is still somewhat cumbersome because of its relatively large size. The multi-dose container is a hypodermic syringe. Contamination problems might arise from the necessity to draw up the injection fluid from a source reservoir thereof into the syringe before loading the dispenser with the syringe.

A different approach, as is described in WO 82/02662, concerns a dose-metering device comprising a fixed screw-threaded member in threaded engagement with a screw-threaded plunger which can be rotated from a manually rotatable cap. Operating this dispenser is a two-handed operation, one hand holding the dispenser and one hand rotating the cap. Two-handed operation is a serious drawback for an injection device, since normally the user employs one hand to press up the skin at the intended injection site.

It is an object of the present invention to provide an improved dose-monitoring dispenser.

BRIEF STATEMENT OF THE INVENTION

The present invention provides a dispensing device suitable for use in dispensing predetermined, in succession quantities of fluid from a reservoir member in the device. The device, as a whole, is formed by an elongated body formed from two separable sections, and optionally, a multipurpose cap.

The elongated body is comprised of a top section containing the functions for mechanically advancing an axially movable piston rod which itself drives a piston plug located inside of the reservoir member so as to express fluid from the reservoir via a needle located at the front or the bottom end of the body. The piston rod which is threaded, advances in successive axial steps of fixed length through rotation of a rotatable piston rod nut whose threads interact with the threads on the piston rod. The piston rod nut is driven by a rotatable worm or screw, which in turn is rotated by advancing axial movement of a pressure device located at the top of the elongated body. The user pushes the pressure device directly or indirectly to dispense the fluid.

A unidirectional transmission system couples the pressure device to a rotatable screw and the screw to the piston rod nut so that the piston rod nut rotates only when the pressure device is pushed into the elongated body.

The elongated body is comprised also of a bottom section, inside of which is the reservoir member and at the bottom end of which is a double-pointed hollow needle with one point extending axially out from the elongated body and the other point extending axially inside the body and into the reservoir member.

The reservoir member is a prefilled replaceable cartridge and, desirably, is a cartridge of a type known in the art which characteristically comprises a (glass) tube sealed at one end by a septum or membrane that is intended to be pierced by the backside end of a hollow double-pointed needle and sealed at the other end by a close-fitting, but slidable plug at the inside of the tube. The plug becomes a piston which travels the length of the tube expelling the fluid from the tube via the needle. When such a cartridge is used as the reservoir member in the bottom section of the elongated body, the needle pierces the septum and the piston rod bears against the slidable plug piston so as to expel the fluid via the needle when and as the piston rod advances. Use of a prefilled, replaceable cartridge as the reservoir member in the dispensing device is advantageous for ensuring that a sterile injection fluid can be administered without need for first transferring fluid from some storage container to the reservoir member.

The cap, when such is part of the dispensing device, is adapted to removable attachment on the bottom section of the elongated body so as to protect the needle, much as a fountain pen cap protects the pen point. In addition, the cap is adapted to removable attachment on the top section of the elongated body. In a preferred mode of this invention, the cap constitutes an operating component of the dispensing device when attached to the top section. A finger-actuated button located at the cap end bears against the pressure device located at the top of the elongated body so that thumb pressure applied to the button forces the pressure device to advance, which movement causes the device to dispense fluid from the reservoir via the needle. When the cap is a working component, the pressure device top can be flush with the top of the elongated tube, thereby protecting against any unintentional advancement thereof (which would expel fluid from the reservoir).

In a preferred mode of the invention, the needle used in the dispensing device is a double-ended needle mounted in a cup-shaped holder, the inside wall of which is threaded so that this needle assembly can be screwed on a threaded portion provided for this purpose at the lower end of the elongated body. Advantageously, the needle assembly can be replaced as necessary from time to time.

According to a preferred embodiment of the invention, the unidirectional transmission system is comprised of: fixed guide means that restrains the pressure device from rotation during its axial advance and retraction movements, and a first locking disc adjacent the inner end of the pressure device and movable therewith through which the screw extends, the screw being stationary, but rotatable. The locking disc and the pressure device contain a pawl system that locks as the pressure device and locking disc advance, so as to force rotation of the screw, and unlocks as the pressure device and locking disc retract, so as to allow rotation of the locking disc on the screw spiral during retraction movement of the locking disc along the screw shank.

The unidirectional transmission system further comprises a second locking disc adjacent the piston rod nut through which the screw extends to its engagement with the piston rod nut for rotating same when the screw rotates. The second locking disk is restrained against rotation movement, as for example, by the fixed guide member. The second locking disc and the piston rod nut contain a pawl system that allows the piston rod nut to be rotated in the desired direction with audible clicks(s) every 90°, 120°, 180° or 360° of rotation, but which locks the piston nut against reverse direction rotation, and derivatively through the piston rod nut locks the screw against the reverse direction rotation.

DETAILED DESCRIPTION OF THE INVENTION

The details of the dispenser device, the best mode of which is illustrated herein, can best be described with reference to the accompanying drawings in which:

FIG. 3 is a section along the line 3—3 on FIG. 2;

FIG. 4 is a fragmentary section along line 4—4 on FIG. 1;

FIGS. 5-9 are respectively sections taken along line 5—5, 6—6, 7—7, 8—8, 9—9 on FIG. 2;

FIG. 10 is an exploded perspective view of the working parts of the dispenser device;

FIG. 11 is a fragmentary perspective view of the piston rod nut showing the driven end thereof;

FIG. 12 is a perspective view of the lower guide member; and

FIG. 13 is a section along line 13—13 on FIG. 10.

Figure 2:
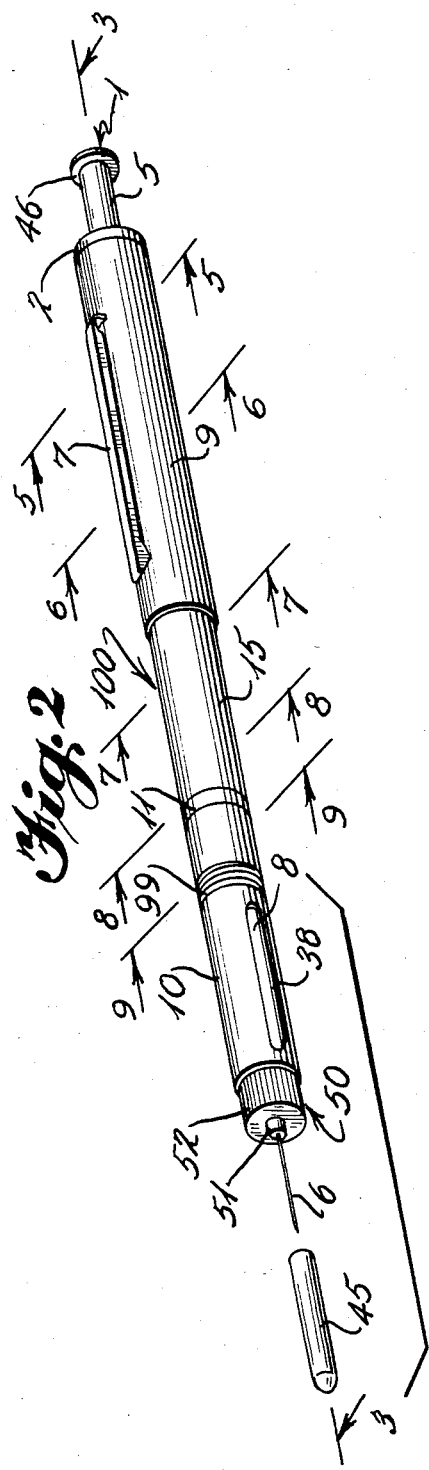
FIG. 2 is a perspective view of the dispenser device with the protective cap on the rear end of the device.

Referring now to FIGS. 2 and 3, the dispenser device of this invention is shown in the ready for use mode with cap 9 positioned on the rear of the elongated body 100 save that the hollow double-pointed needle 6 remains protected by a needle housing or cap 45.

The dispenser comprises a needle assembly 50 removably mounted at the forward end of the dispenser device, such assembly comprising needle housing 45, a plug 51 in which the needle 6 is fixed and through which needle 6 extends and a cup-like holder 52 of which plug 51 is a part, threaded on the inside wall thereof. Needle cap 45 seats on plug 51. Desirably, needle housing 45 is retained on the needle plug 51 through a friction grip so the user can pull off needle housing 45 just prior to using the dispenser device, and push needle housing 45 back on immediately after use.

Figure 1:
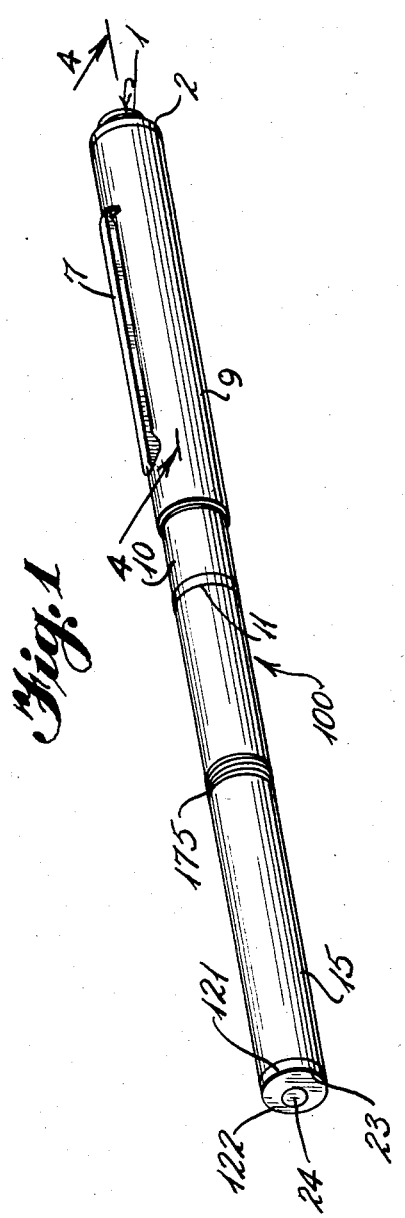
FIG. 1 is a perspective view of the dispenser device with the protective cap over the needle.

The elongated body 100 of the dispenser device contains threads 175 thereon to which internally threaded cap 9 may be secured for proper positioning at the rear or top end of elongated body 100 (see FIG. 1). A like set of threads 99 are provided on body 100 appropriately near the front or bottom needle end (see FIG. 2) so that cap 9 may be secured on the front end of body 100, for a storage position arrangement of the dispenser device which protects needle 6 and for that matter needle housing 45 against damage and contamination when the dispenser is not in use.

The elongated body 100 is formed from assembly of two readily separated sections: a top section 15 containing therein the means elements that function to advance a piston 18 axially forward toward needle 6; and a bottom section 10 containing therein the fluid reservoir and on which needle 6 is mounted. In the illustrated embodiment, these two sections, 10 and 15, are screwed together through the intermediary of a threaded sleeve 11. As is illustrated in FIG. 3, the fluid reservoir is in the form of a prefilled cartridge 8 that may be removed and replaced when sections 10 and 15 are separated. Sections 10 and 15 are separated relatively often for replacing used cartridges with new cartridges, but sleeve 11 may well remain attached to top section 15 for the entire useful life of the dispenser device.

At its front end, the tubular prefilled cartridge 8 is sealed by a (rubber) membrane or septum 120, through which the rear of hollow double-pointed needle 6 has pierced. At its back end the tubular prefilled cartridge 8 is sealed by a close fitting (rubber) plug 25 that is free to slide forward. Plug 25 constitutes a piston that will be forced forward inside of cartridge 8 by movement of piston rod 18, thereby expelling the fluid contents of a fresh cartridge 8 through needle 6. As will be explained hereinafter in more detail, the advancing or forward movement of piston rod 18 (to expel fluid through needle 6) is generated by rotation of a worm or screw 19 to turn a piston rod nut 17 with which the screw is engaged and which (see FIG. 10) contains threads 98 interengaging and interacting with corresponding threads 97 located on the piston 18.

Referring now to FIG. 10, it may be seen that at the upper or rear end of top section 15, forming the upper end face thereof is a movable pressure responsive means element 24, hereinafter termed the pressure device, which generally resembles an inverted cup, and whose detailed structure is illustrated in FIG. 10. Pressure device 24 is slidably retained in section 15 by a fixed guide member 23, herein identified as the first or upper guide member, the detailed structure of this first guide member 23 further being illustrated in FIG. 13. In the rest position for the dispenser device, as is illustrated in FIG. 1, the top of pressure device 24 is essentially flush with the top surface of body section 15, and for forward movement to expel fluid through needle 6, pressure device 24 must be pushed longitudinally into top section 15. This arrangement is believed to be advantageous for reason that during storage or non-use of the dispenser device, the usual location for cap 9 is on the front end of elongated body 100 around lower body section 10 protecting needle 6, which is to say, that the pressure device actuator 24 of the dispenser device is exposed. Allowing pressure device 24 to project from top section 15 or providing a locking arrangement to secure the pressure device 24 flush but in a fully depressed (rather than rest) position could be done, but neither is considered to be a desirable expedient.

The pressure device 24 is constrained by fixed guide 23 to longitudinal or axial movement. As may be seen in FIGS. 3 and 13, longitudinal ribs or axial projections 26 on pressure device 24 ride in the longitudinal grooves 27 located in the inside wall of guide member 23 thereby preventing rotation of pressure device 24 but allowing forward and back axial movement by the pressure device 24 inside of fixed guide 23. FIG. 10 shows also how the bottom surface of pressure device 24 is formed into a pawl system half 28b that constrains rotation of the hereinafter described upper or first lock disc 22 to unidirectional rotation, and, as is described hereinafter, prevents lock disc 22 from rotating as pressure device 24 and lock disc 22 move forward.

At the bottom of guide member 23 are provided slots 39 in which the ears 35 on the hereinafter described lower or second lock disc 20 ride. A roughened surface is formed in the inner wall of body section 15, (not shown) for fixedly securing guide member 23 inside body section 15.

Illustrated best in FIGS. 10 and 13 is the peripheral shoulder 121 on guide 23 that seats on the top edge of body section 15. The face of guide 23 constitutes the top surface of the dispenser device body 100 with the top of pressure device 24 being a centerpiece that is flush or minimally depressed from the top face 122 (see FIG. 1).

Referring again now to FIGS. 10 and 3, it may be seen that the first or upper lock disc 22 is located at the underside of pressure device 24 in contact therewith at pawl portion 28b. A conical spring 21 presses against the underside of lock disc 22, thereby spring biasing lock disc 22 and pressure device 24 toward the rear of body section 15 to their rest position. Forward movement of pressure device 24 must overcome the bias of spring 21.

A spiral worm or screw 19 extends down i.e., forward, from a free end in the central cavity of pressure device 24 through lock disc 22 to a screw tip engagement with piston rod nut 17. Screw 19 is illustrated as spiraling 180° from the free end thereof to the engaged screw tip end. Screw 19 extends through a second lock disc 20 as well.

As already has been pointed out, the second lock disc 20 is located near the bottom or forward end of the fixed guide member 23 with tabs 35, riding in the guide member slots 39. The resilient conic spring 21 maintains lock discs 20 and 22 spaced apart in the rest position of the dispenser device holding first lock disc 22 on the pawl system 28a,b and holding second lock disc 20 on a hereinafter described pawl system 34a,b.

The detailed structure of first lock disc 22, spiral screw 19 and second lock disc 20 which now will be described are illustrated respectively by FIGS. 3 and 5 through 10.

First lock disc 22 is a circular member configured on one surface with pawl half 28a to match the pawl half 28b on the bottom surface of pressure device 24. A rectangular slot or bore opening 29 is provided at the center of lock disc 22. The upper portion 30 of spiral screw 19 extends through slot opening 29 to the cavity inside of pressure device 24. Upon axial advancing movement of pressure device 24, the fixed-in-place screw 19 extends further into the cavity, but can pass through slot 29 of lock disc 22 only if the screw 19 turns in conformity with its spiral shape, or else the lock disc 22 turns on the spiral shank of screw 19. Which member will rotate is determined by pawl system 28a,b; the pawl system 28a,b forces screw 19 to rotate on advancement movement by disc 22.

At the tip end of screw 19 is a pair of ears 31 sized for a fit with a slot 32 in the hereinafter described piston rod nut 17 so as to drive piston rod nut 17. The second lock disc 20 is located on the shank of screw 19 just above the ears 31 facing, so to speak, lock disc 22 and the pressure device member 24 (see FIG. 10) and spaced apart therefrom by spring 21. The second lock disc 20 is provided with a central circular aperture 40 through which the shank of spiral screw 19 passes and in which screw 19 can rotate freely. Formed in the underface of second lock disc 20 is a pawl system half 34a. From the sides of lock disc 20 extend the tabs or protuberances 35 that seat in and ride slots 39 on the fixed-in-place guide member 23, thereby constraining second lock disc 20 against rotational movement. Second lock disc 20 may move longitudinally in slots 39. Accordingly, the pawl half 34a on lock disc 20 cooperates with a pawl half 34b on the top of piston rod nut 17 (see FIG. 11) to allow only unidirectional rotation by the piston rod nut 17. Since the ears 31 at the tip end of screw 19 are seated in the slot 32 on piston rod nut 17, screw 19, too, is constrained to unidirectional rotation by the pawl system 34a,b. Locking contact between the pawl halves 34a, 34b is maintained by the force of spring 21 and, of course, causes disc 20 to hold the screw tip ears 31 engaged in slot 32.

When pressure device 24 is pushed forward, spring 21 compresses. Since the spring pressure holds the pawl half 28b on pressure device 24 and pawl half 28a on lock disc 22 in locked position, spiral screw 19 is forced to rotate in the rectangular slot 29 as lock disc 22 rides down i.e., advances along the shank of spiral screw 19. In turn, the screw tip ears 31 rotate piston rod nut 17, such being the unidirectional movement allowed by pawl system 34a,b. Then, when pressure on pressure device 24 is released, spring 21 causes retraction movement of pressure device 24. However, pawl system 34a,b locks piston rod nut 17 and prevents reverse direction rotation of screw tip ears 31 locking thereby the spiral screw 19 against reverse direction rotation. First lock disc 22 is free to rotate in the reverse direction, such being the unidirectional movement allowed by pawl system 28a,b. Therefore, during retraction movement of pressure device 24, spiral screw 19 is locked, but lock disc 22 rotates allowing the rectangular slot 29 therein to ride up i.e., so as to retract lock disc along the shank of screw spring 19, together with pressure device 24.

Allusion has already been made to piston rod nut 17, and to presence thereon of the pawl half 34b and of slot 32 for generating unidirectional rotation. The detailed structure of the piston rod nut 17 is illustrated by FIGS. 10 and 11, reference now being made thereto. Shown in FIG. 11 is that both slot 32 and pawl half 34b are formed in the top or rearmost surface of a longitudinally extended tubular member. Piston rod nut 17 is adapted to fit rotatably inside of a fixed sleeve 16 in top section 15 of the dispenser device body 100. The forward portion of piston rod nut 17 is slit or bifurcated by longitudinal slots 33, four slots being illustrated, and the resulting legs 17' at the forward end of piston rod nut 17 are given a spread apart bias (spring type), as is illustrated in FIG. 10. On the bottom or forward split ends of piston rod nut 17 are beveled surfaces 41. The lower or forward portion of the legs 17' on the piston rod nut 17 are internally threaded at 98.

As may be seen in FIGS. 3 and 10 piston rod nut 17 is rotably secured at the intended location inside top body section 15 between fixed sleeve 16 and the bottom of fixed guide 23. A fixed stop ring 14 is located at the lower end of sleeve 16. A movable guide member 13, termed the lower guide, is located in body section 15 beneath i.e., forward of stop ring 14. The detailed structure of guide 13 is illustrated in FIGS. 10 and 12. The lower guide 13 serves to clamp the internal threads 98 at the lower portion of the legs 17' onto piston rod nut 17 matching with threads 97 on piston rod 18 through a camming cooperation between the beveled surfaces 41 on piston rod nut 17 and a conic surface 37 on guide 13.

Lower guide 13 is free to move longitudinally into and out of camming contact with the legs 17' on piston rod nut 17. A pair of slots 125 in the periphery of guide 13 ride on ribs 124 that are part of stop ring 14 serving thereby to allow longitudinal movement of guide 13 but not rotation. In the fully assembled body 100 guide 13 is pressed up against the legs 17' of piston rod nut 17 by the top rim of cartridge 8 camming legs 17' into a clamp on piston rod 18, all as is illustrated in FIG. 3. However, when the body sections 10 and 15 are separated, guide 13 shifts longitudinally (forward), thereby allowing the legs 17' on piston rod 17 to spread themselves apart, which releases piston rod 18. For example, guide 13 may be allowed 0.5 mm of axial longitudinal movement, after which it comes to rest on sleeve 11.

The piston rod 18 is inside of piston rod nut 17, concentric therewith and extending past the bottom thereof. The lower guide 13 serves as a guide member for piston rod 18. Piston rod 18 extends through the central aperture 36 in guide 13 (see FIG. 9). By appropriate shaping of aperture 36 and by providing a like cross-section shape for piston rod 18, for example, flat sides and circular threaded arc ends, piston rod 18 is allowed axial movement through guide 13, but rotational movement therein is prevented. Parenthetically, it is noted that presence of flat sides on a threaded otherwise circular piston rod 18 does not prevent advancement of the piston rod 18 by rotation of (threaded) piston nut 17 on the piston rod threads.

A top boss 130 prevents piston rod 18 from falling out through guide 13. At the bottom terminus of piston rod 18 is a thrust pad 12 adapted to fit inside the tube of cartridge 8. Thrust pad 12 pushes against the plug 25 in cartridge 8, moving same to expel the fluid contents of cartridge 8 through needle 6 as the piston 18 is advanced.

The dispenser device is adapted to use with cartridges 8 and needles 6 that are provided as separate removable components, which is a practical convenience. Cartridges empty rapidly and must be replaced frequently. Needles, too, must be replaced frequently, but not necessarily as often as the cartridges. The cartridge 8 slips into the central cavity of body section 10 without more, septum 120 face front so plug 25 will face pad 12 at the end of piston rod 18. An aperture 110 (see FIG. 3) is provided centrally of the front face of section 10 for passage of needle 6 therethrough (and then through the cartridge septum 120). In addition, the front end portion of section 10 is externally threaded at 111, and in the mode herein illustrated is reduced in diameter as well. The needle assembly 50 seats on the threads 111. As has already been indicated, replacement needles are provided in the form of the assembly 50 which, to repeat, comprises a hollow double pointed needle 6 embedded firmly in a plug 51 centered in an internally threaded cup 52 that screws on to the front of body section 10. The removable needle housing 45 is, of course, part of needle assembly 50.

The cap 9 serves a dual function, first of protection for the relatively fragile needle 6 when cap 9 is placed on the needle end of body 100 at threads 99 on body section 10 (see FIG. 4). For compactness, needle housing 45 fits inside of the tube 5 hereinafter described. A clip 7 on cap 9 allows the dispenser device to be clipped to a user's pocket.

The second function served by cap 9 is as the locale for the operating actuator of the dispenser device. Referring now to FIGS. 2, 3 and 4, the actuator mechanism is located at the closed end of cap 9 and the presence thereof is largely concealed except when cap 9 has been secured to the top or rear end of elongated body 100. The applicator or actuator 1 comprises a button top 46 that is near to coextensive with the top face 2 of cap 9, and attached to button 46 is a tube 5, which extends into cap 9. A recess 42, between the outside wall of tube 5 and the inside wall of a fixed guide 4 inside cap 9, is provided by the underside of the top face 2 of cap 9 and a peripheral flange 43 on tube 5. A relatively weak spring 3 is located in recess 42. Ordinarily, spring 3 will maintain applicator 1 in its button down position with button 46 abutting face 2, and such happens when cap 9 is mounted on the needle end of elongated body 100 as is illustrated by FIG. 4.

When cap 9 is screwed on top section 15, as shown in FIGS. 2 and 3, its appearance changes. Spring 21 is much stronger than spring 3, which means that spring 3 is compressed to force button 46 to extend out of the cap to the position illustrated by FIGS. 2 and 3, which is then the rest position for applicator 1. The end of tube 5 becomes centered in the top opening of the fixed upper guide 23 in contact with the top of (movable) pressure device 24. Forward travel by the applicator 1, particularly of tube 5 is from this rest position to the previous button down position where flange 43 on tube 5 contacts rim 44 on fixed guide 4 inside of cap 9.

OPERATION OF THE DISPENSER DEVICE

The drawing hereof illustrates a best mode of the dispenser device at about 1.5 X scale, FIG. 3 showing the dispenser device ready for use once needle housing 45 is removed. Immediately after use, needle cap 45 would be returned. FIG. 3 can be considered to illustrate the dispenser device with a cartridge 8 and needle 6 about to be replaced, except that then piston rod 18 would be fully extended into cartridge 8. A window 38 is provided so the user knows when cartridge 8 has been emptied. Description of how the dispenser device operates commences from a depleted cartridge state, and when a new needle is required.

Needle assembly 50 is unscrewed and discarded and if such is desired, a new needle assembly may be screwed on to the front end of section 10 immediately. Somewhat to be preferred, however, would be to do so after a new cartridge 8 is in place.

The body sections 10 and 15 are unscrewed separating them, which then exposes the top of cartridge 8 so that it may be lifted out of body section 10 and discarded. When a new cartridge 8 is inserted in section 10, full insertion thereof causes the backside of needle 6 to pierce the cartridge septum 120. If a new needle is added after body 100 has been reassembled, screwing needle assembly 50 on threads 111 causes needle 6 to pierce septum 120.

Once sections 10 and 15 are separated, the guide 13 drops away from its clamping position against the legs 17' of piston nut 17, allowing legs 17' to spread apart to release piston rod 18. Piston rod 18, which up to then has been in a fully advanced position, can now be pressed back to its starting position e.g., by the user's finger.

Once a fresh cartridge 8 is in bottom section 10, the elongated body 100 may be reassembled by screwing sections 10 and 15 together (via sleeve 11). If the user has not already done so, piston rod 18 would be pushed back to its starting position by engagement of plug 25 against piston rod pad 12 as sections 10 and 15 are being brought together. The tubular end of cartridge 8 fits in the annular space between piston rod 18 and the inside wall of sleeve 11 (which is adapted to remain on and form part of section 15), and cartridge 8 must be so placed before the sections 10 and 15 can be joined. Then as sections 10 and 15 are joined (by screwing them together), the circular rim of cartridge 8 forces guide 13 up into camming engagement with beveled surfaces 41 on the legs 17' of piston rod nut 17, clamping piston rod 18 on the legs 17' with threads 97 and 98 engaged, the position illustrated by FIG. 3.

Desirably, at the fully retracted position for piston rod 18, complete assembly of sections 10, 15 has caused piston rod 18 to move plug 25 slightly forward into cartridge 8, e.g., ½ mm. This small movement fills needle 6 with injection fluid from the cartridge, ensuring a subsequent air-free dispensing of fluid.

Conveniently, cap 9 may be left on the top of section 15 during disassembly and reassembly of elongated body 100. Then the dispenser device is ready for use. To actually dispense fluid, the user repetitively depresses, then releases the button 46 of applicator 1. Travel distance per stroke is determined by the spacing along tube 5 between flange 43 thereon and the rim 44 of guide 4. In turn, pressure device 24 advances the same distance (against spring 21) forcing screw 19 to rotate, thereby rotating also the piston rod nut 17, and advancing piston rod 18 to push plug 25 forward. A predetermined and precisely known quantity of the injection fluid is expelled from cartridge 8 during this one forward stroke. The user can measure out the requisite dose by counting how many times the button 46 of applicator 1 is pushed. In addition, provision has been made for an audible signal. A distinct clicking sound can be heard whenever pawl half 34a rides over pawl half 34b, which sound is intended to assure the user that the fluid is indeed being injected and to aid in counting out the injection dose.

As should be apparent from the above description, the dispenser device of this invention provides an easily operated system for dispensing a predetermined quantity of a medicine with high accuracy. An air-free injection system is ensured. The problems that have been encountered with dispensers of similar type known heretofore are avoided. Furthermore, the dispenser is secure against an accidental activation movement of applicator 1 when the protecting cap 9 is screwed on the needle end, since the applicator button is then both concealed and located opposite the working section of the dispenser. Pressure device 24 is flush with the top of section 15.

Finally, the dispenser device may be made of corrosion resistant and wear-resisting material, for instance, chromium-plated brass, stainless steel and high-strength plastics, all of which provide a high degree of structural stability and durability for the dispenser device components.

We claim:

1. A dispenser device for dispensing predetermined successive quantities of fluid through a needle which comprises an elongated body adapted for placement of a double-pointed hollow needle at one end thereof;

said elongated body further comprising separable top and bottom longitudinal sections secured together, the bottom section having a reservoir region adapted to contain therein a prefilled reservoir to serve as fluid reservoir for dispensing the fluid therefrom;

a needle placement locale on the bottom section whereby a double-pointed hollow needle situated thereon would extend into the region for the prefilled reservoir and into the fluid of any reservoir in said region;

the top section containing the dispensing mechanism of:

a non-rotatable pressure responsive means element adapted to be pushed longitudinally inward from outside of said body, advancing same longitudinally in said body; a stationary rotatable screw operatively connected to said pressure responsive means element and rotated by advancing movement of said element; a stationary rotatable piston rod nut operatively connected to said rotatable screw and rotated by said rotatable screw and a non-rotatable piston rod threaded to said piston rod nut and advanced by rotation of said piston rod nut;

spring means adapted to cause said pressure responsive means element to retract when pushing pressure thereon ceases; and means adjacent the connection between said screw and said piston rod nut for preventing reverse rotation of said screw during retraction movement of said element;

said piston rod extending into the region for the prefilled reservoir whereby advancing movement of said piston rod could expel fluid from a reservoir in said region.

2. The dispenser device of claim 1 containing therein a reservoir that comprises a prefilled sealed cartridge in the form of a liquid filled tube having a septum at one end, said septum being pierceable by a double-pointed hollow needle and a slidable plug in the tube at the other end;

said reservoir being insertable only when the top and bottom sections are separated, assembly of said top and bottom sections with a prefilled reservoir therein generating contact of the piston rod with said plug, whereby advance of said piston rod will force said plug forward and expel fluid from said cartridge.

3. The dispenser device of claim 2 further including a needle assembly mounted on the elongated body, said needle assembly further comprising a double-pointed hollow needle, an internally threaded cup through the base of which said needle extends, and wherein said needle is firmly secured, the needle end of said elongated body being externally threaded, whereby said needle assembly is removably secured on to said body, and optionally, a removable housing around the needle protecting same, assembly of said top and bottom sections generating also sufficient piston rod induced forward movement of said plug to expel fluid into said needle displacing air therefrom.

4. The dispenser device of claim 1 further comprising a pressure responsive means element located essentially flush to the top end of said elongated body, depressable longitudinally inside the elongated body for causing the advancement of said piston rod.

5. The dispenser device of claim 4 further comprising a multipurpose cap member, said cap member being adapted for placement on the needle end of said elongated body so as to be protective of any needle thereon, and, alternatively, on the top end of said body at which location said cap member is superposed on the pressure responsive means element and constitutes a longitudinal extension thereof;

an applicator on said cap adapted to be pressed by a user's finger then being in bearing contact with said pressure responsive means element, whereby finger pressure on said applicator causes the applicator to push against said pressure responsive means element advancing said element for causing the advancement of said piston rod as aforesaid.

6. The dispenser device of claim 1 wherein the stationary rotatable piston rod nut comprises a tubular member a portion of which is split into a multitude of biased-apart and internally threaded legs, the piston rod having thereon external threads corresponding to the aforementioned threads on the legs of said piston rod nut, the stationary rotatable piston rod being located inside the piston rod nut, freely movable relative to the piston rod nut when the two body sections are separated, and means in said elongated body section that clamp the internally threaded legs of said piston rod nut to the externally threaded piston rod when the two body sections are joined to form said elongated body, so that the piston rod advances when the piston rod nut rotates, the piston rod being retractable when the body sections are separated.

7. The dispenser device of claim 6 wherein the means for clamping the internally threaded legs of said piston rod nut to said piston rod comprises a guide through which the piston rod extends adapted to prevent rotation of the piston rod, said guide being movable between a clamping location when the two body sections are joined, and a non-clamping location when the two body sections are separated.

8. The dispenser device of claim 7 wherein said movable guide is adapted to be moved from non-clamping location to clamping location by the end of a prefilled reservoir when such is present in said elongated body.

9. The dispenser device of claim 1 wherein the means for preventing reverse rotation of said screw is a unidirectional transmission system comprising:

a first lock disc associated with said pressure responsive means element during advancement and retraction longitudinal movement, the association including a pawl system set to secure said element and first lock disc against relative rotation during advancing movement of said element and lock disc, to allow rotation of said first lock disc upon retraction movement;

said screw extending through said first lock disc so as to require rotation by said screw upon advance of said element during which said first lock disc advances along the shank of said screw, said first lock disc thereby being caused to rotate during retraction movement along the shank of said screw;

a second and stationary lock disc associated with said screw and said piston rod nut adjacent the connection between said screw and said piston rod nut, through which said screw extends to a driving connection with said piston rod nut, said second lock disc and said piston rod nut being associated by a pawl system set to allow rotation of the screw during advancement of said pressure responsive means element thereby rotating said piston rod nut, and to secure said piston rod nut against reverse rotation, whereby upon retraction movement of said pressure element during which said first lock disc retracts along the shank of said screw, the pawl system of said second lock disc prevents rotation of said piston rod nut and thereby of said screw, forcing the rotation of said first lock disc as aforesaid, the aforesaid spring means maintaining said first and second lock discs in their pawl system association contact with said element and piston rod nut respectively.

10. The dispenser device of claim 9 wherein the pawl system associated with said second lock disc and piston rod nut is adapted to generate an audible sound upon rotation of said piston rod nut, whereby the user of the dispenser device may be made aware when fluid is being dispensed therefrom.

* * * * *